United States Patent [19]

Nagao et al.

[11] Patent Number: 5,496,710

[45] Date of Patent: Mar. 5, 1996

[54] PROTEASE

[75] Inventors: Hiromasa Nagao, Kanagawa; Takashi Yoneya, Tokyo; Toshio Miyake, Kanagawa; Atsuo Aoyama, Kanagawa; Ken-ichi Kai, Kanagawa; Shun-ichi Kidokoro, Kanagawa; Yoichiro Miki, Kanagawa; Kimiko Endo; Akiyoshi Wada, both of Tokyo, all of Japan

[73] Assignees: Sagami Chemical Research Center, Tokyo, Japan; Holland Sweetner Company V.O.F., Netherlands

[21] Appl. No.: 38,932

[22] Filed: Mar. 29, 1993

[30] Foreign Application Priority Data

Jun. 8, 1992 [JP] Japan ................................... 4-171479
Aug. 14, 1992 [JP] Japan ................................... 4-237606
Sep. 18, 1992 [JP] Japan ................................... 4-273413

[51] Int. Cl.$^6$ .......................... C12S 3/14; C12S 13/00; C12P 7/62

[52] U.S. Cl. .................... 435/68.1; 435/212; 435/219; 435/220; 435/221

[58] Field of Search .................. 435/68.1, 212, 435/219, 220, 221

[56] References Cited

FOREIGN PATENT DOCUMENTS 0418625  3/1991  Germany.

OTHER PUBLICATIONS

Shigetoshi Endo, "Studies on Protease Produced by Themophilic Bacteria", J. Fermentation Technology, 1962, vol. 40, pp. 346–353.
Titani et al., "Amino–acid Sequence of Thermolysin", Nature New Biology, Jul. 12, 1972, vol. 238, pp. 35–37.
Titani et al., "Amino Acid Sequence of Thermolysin. Isolation and Characterization of the Fragments Obtained by Cleavage with Cyanogen Bromide", Biochemistry, 1972, vol. 11, No. 13, pp. 2427–2435.
Holmes et al., "Structure of Thermolysin Refined at 1–6 A Resolution", J. Mol., Biol., 1982, vol. 160, pp. 623–639.
Kubo et al., "Cloning and Nucleotide Sequence of the Highly Thermostable Neutral Protease Gene from *Bacillus stearothermophilus*", J. General Microbiology, 1988, vol. 134, pp. 1883–1892.
Vandeyar et al., "A simple and rapid method for the selection of oligodeoxynucleotide–directed mutants", Gene, 1988, vol. 65, pp. 129–133.
Kubo et al., "mRNA Secondary Structure in an Open Reading Frame Reduces Translation Efficiency in *Bacillus subtilis*", Journal of Bacteriology, Jul. 1989, vol. 171, No. 7, pp. 4080–4082.
Higuchi et al., "A general method of in vitro preparation and specific mutagenesis of DNA fragments: study of protein and DNA interactions", Nucleic Acids Research, 1988, vol. 16, No. 15, pp. 7351–7367.
Toma et al., "Effect of Glu–143 and His–231 substitutions on the catalytic activity and secretion of *Bacillus subtilis* neutral protease", Protein Engineering, 1989, vol. 2, No. 5, pp. 359–364.
Eijsink et al., "Introduction of a stabilizing 10 residue β–hairpin in *Bacillus subtilis* neutral protease", Protein Engineering, 1992, vol. 5, No. 1, pp. 157–163.
Eijsink et al., "Increasing the thermostability of a neutral protease by replacing positively charged amino acids in the N–terminal turn of α–helices", Protein Engineering, 1992, vol. 5, No. 2, pp. 165–170.
Margarit et al., "Cumulative stabilizing effects of glycine to alanine substitutions in *Bacillus subtilis* neutral protease", Protein Engineering, 1992, vol. 5, No. 6, pp. 543–550.
Inouye, "Effects of Salts on Thermolysin: Activation of Hydrolysis and Synthesis of N–Carbobenzoxy–L–Aspartyl–L–Phenylalanine Methyl Ester, and a Unique Change in the Absorption Spectrum of Thermolysin", J. Biochem., 1992, vol. 112, pp. 335–340.
Wang et al., "Expression of *Bacillus subtilis* neutral protease gene (nprE) in *Saccharomyces cerevisiae*", Journal of General Microbiology, 1993, vol. 139, pp. 343–347.
Hardy et al., "Stabilization of *Bacillus stearothermophilus* neutral protease by introduction of prolines", FEBS Letter, 1993, vol. 317, No. 1.2, pp. 89–92.
Kubo et al., "Alteration of Specific Activity and Stability of Thermostable Neutral Protease by Site–Directed Mutagenesis", Applied and Environmental Microbiology, Nov. 1992, vol. 58, No. 11, pp. 3779–3783.
Imanaka et al, "A New Way of Enhancing the Thermoplastability of Proteases", Nature, vol. 324, No. 6098, Dec. 1986, pp. 695–697.
Derwent Publications Ltd., AN 93–022706 & JP–A–4 349 883, Database WPI, Section CH, Week 9303, Dec. 1992.
Kostrov et al, Biosis Reviews, AN 87130218, vol. 23, No. 1, pp. 255–256.
Eijsink et al, Protein Engineering, vol. 5, No. 5, 1992, pp. 421–426.
Imanaka, Annuals of the New York Academy Science, vol. 613, 1990, pp. 347–351.

*Primary Examiner*—Margaret Parr
*Assistant Examiner*—Bradley L. Sisson
*Attorney, Agent, or Firm*—Cushman Darby & Cushman

[57] ABSTRACT

A modified protease is disclosed, which is a mutant of the thermostable neutral protease wherein at least one amino acid residue of SEQ ID NO: 1 selected from the group consisting of the 144th leucine residue, the th aspartic acid residue, the 187th glutamic acid residue and the 227th asparagine residues is replaced with an amino acid residue other than said amino acid.

8 Claims, 9 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 316 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:1:

```
Ile  Thr  Gly  Thr  Ser  Thr  Val  Gly  Val  Gly  Arg  Gly  Val  Leu  Gly  Asp
 1                  5                          10                         15

Gln  Lys  Asn  Ile  Asn  Thr  Thr  Tyr  Ser  Thr  Tyr  Tyr  Leu  Gln  Asp
              20                           25                      30

Asn  Thr  Arg  Gly  Asn  Gly  Ile  Phe  Thr  Tyr  Asp  Ala  Lys  Tyr  Arg  Thr
          35                          40                    45

Thr  Leu  Pro  Gly  Ser  Leu  Trp  Ala  Asp  Ala  Asp  Asn  Gln  Phe  Phe  Ala
      50                      55                          60

Ser  Tyr  Asp  Ala  Pro  Ala  Val  Asp  Ala  His  Tyr  Tyr  Ala  Gly  Val  Thr
65                       70                       75                         80

Tyr  Asp  Tyr  Tyr  Lys  Asn  Val  His  Asn  Arg  Leu  Ser  Tyr  Asp  Gly  Asn
                  85                       90                       95

Asn  Ala  Ala  Ile  Arg  Ser  Ser  Val  His  Tyr  Ser  Gln  Gly  Tyr  Asn  Asn
                100                      105                      110

Ala  Phe  Trp  Asn  Gly  Ser  Gln  Met  Val  Tyr  Gly  Asp  Gly  Asp  Gly  Gln
          115                      120                      125

Thr  Phe  Ile  Pro  Leu  Ser  Gly  Gly  Ile  Asp  Val  Val  Ala  His  Glu  Leu
      130                      135                      140

Thr  His  Ala  Val  Thr  Asp  Tyr  Thr  Ala  Gly  Leu  Ile  Tyr  Gln  Asn  Glu
145                      150                           155                      160
```

| Ser | Gly | Ala | Ile | Asn | Glu | Ala | Ile | Ser | Asp | Ile | Phe | Gly | Thr | Leu | Val |
|---|---|---|---|---|---|---|---|---|---|---|---|---|---|---|---|
| | | | | 165 | | | | | 170 | | | | | 175 | |

| Glu | Phe | Tyr | Ala | Asn | Lys | Asn | Pro | Asp | Trp | Glu | Ile | Gly | Glu | Asp | Val |
|---|---|---|---|---|---|---|---|---|---|---|---|---|---|---|---|
| | | | 180 | | | | | 185 | | | | | 190 | | |

| Tyr | Thr | Pro | Gly | Ile | Ser | Gly | Asp | Ser | Leu | Arg | Ser | Met | Ser | Asp | Pro |
|---|---|---|---|---|---|---|---|---|---|---|---|---|---|---|---|
| | | 195 | | | | | 200 | | | | | 205 | | | |

| Ala | Lys | Tyr | Gly | Asp | Pro | Asp | His | Tyr | Ser | Lys | Arg | Tyr | Thr | Gly | Thr |
|---|---|---|---|---|---|---|---|---|---|---|---|---|---|---|---|
| | 210 | | | | | 215 | | | | | 220 | | | | |

| Gln | Asp | Asn | Gly | Gly | Val | His | Ile | Asn | Ser | Gly | Ile | Ile | Asn | Lys | Ala |
|---|---|---|---|---|---|---|---|---|---|---|---|---|---|---|---|
| 225 | | | | | 230 | | | | | 235 | | | | | 240 |

| Ala | Tyr | Leu | Ile | Ser | Gln | Gly | Gly | Thr | His | Tyr | Gly | Val | Ser | Val | Val |
|---|---|---|---|---|---|---|---|---|---|---|---|---|---|---|---|
| | | | | 245 | | | | | 250 | | | | | 255 | |

| Gly | Ile | Gly | Arg | Asp | Lys | Leu | Gly | Lys | Ile | Phe | Tyr | Arg | Ala | Leu | Thr |
|---|---|---|---|---|---|---|---|---|---|---|---|---|---|---|---|
| | | | 260 | | | | | 265 | | | | | 270 | | |

| Gln | Tyr | Leu | Thr | Pro | Thr | Ser | Asn | Phe | Ser | Gln | Leu | Arg | Ala | Ala | Ala |
|---|---|---|---|---|---|---|---|---|---|---|---|---|---|---|---|
| | | 275 | | | | | 280 | | | | | 285 | | | |

| Val | Gln | Ser | Ala | Thr | Asp | Leu | Tyr | Gly | Ser | Thr | Ser | Gln | Glu | Val | Ala |
|---|---|---|---|---|---|---|---|---|---|---|---|---|---|---|---|
| | 290 | | | | | 295 | | | | | 300 | | | | |

| Ser | Val | Lys | Gln | Ala | Phe | Asp | Ala | Val | Gly | Val | Lys |
|---|---|---|---|---|---|---|---|---|---|---|---|
| 305 | | | | | 310 | | | | | 315 | |

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: Other nucleic acid (synthetic DNA)

( x i ) SEQUENCE DESCRIPTION: SEQ ID NO:2:

CCAGATTGGC AAATTGGAGA G                            21

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: Other nucleic acid (synthetic DNA)

( x i ) SEQUENCE DESCRIPTION: SEQ ID NO:3:

CGCAAGATCA TGGCGGGG                               18

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: Other nucleic acid (synthetic DNA)

( x i ) SEQUENCE DESCRIPTION: SEQ ID NO:4:

AACGCATGCG GTAACCAATT ATACAGC                     27

( 2 ) INFORMATION FOR SEQ ID NO:5:

( i ) SEQUENCE CHARACTERISTICS:
        ( A ) LENGTH: 27 base pairs (B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO:5:

AACGCATGCG GTAACCCATT ATACAGC    27

(2) INFORMATION FOR SEQ ID NO:6:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: Other nucleic acid (synthetic DNA)

(xi) SEQUENCE DESCRIPTION: SEQ ID NO:6:

AACGCATGCG GTAACCAAAT ATACAGC    27

(2) INFORMATION FOR SEQ ID NO:7:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: Other nucleic acid (synthetic DNA)

(xi) SEQUENCE DESCRIPTION: SEQ ID NO:7:

GAGATACCAC TTTATTTCAC CCCT    24

PROTEASE

FIELD OF THE INVENTION

This invention relates to novel thermolysin-like neutral metallo-proteases and to use thereof, more specifically in the production of benzyloxycarbonyl-α-L-aspartyl-L-phenylalanine methyl ester.

Thermolysin is a useful enzyme which is commercially available and used in a wide variety of fields, for example in detergent compositions, in food processing and in cosmetic formulations. It is further used in the synthesis of benzyloxycarbonyl-α-L-aspartyl-L-phenylalanine methyl ester (hereinafter referred to briefly as Z-APM), which is a precursor of aspartame, an artificial sweetener.

BACKGROUND OF THE INVENTION

Thermolysin was first found in the culture broth of *Bacillus thermoproteolyticus* (Endo, S. (1962) J. Fermentation Tech., 40, 346–353) and a number of investigations have been conducted thereon. Thus, for instance, its amino acid sequence (Titani, K., et al., (1972) Nature New Biol., 238, 35–37) and the three-dimensional structure of the enzyme (Holmes, M. A. and Matthews, B. W., (1982) J. Mol. Biol. 160., 623–639) have been elucidated. Meanwhile, the protease gene was cloned from *Bacillus thermoproteolyticus* (EP-A-0418625) and the amino acid sequence of the mature enzyme as deduced from the nucleotide sequence of said gene was found to be different from the original primary structure as indicated by Titani in two positions. Thus, it was reported that the 37th (from the amino terminal) amino acid residue of the mature enzyme is not aspartic acid but asparagine and the 119th one is not glutamic acid but glutamine. This amino acid sequence is identical with that coded by nprM, one of the protease genes cloned from *Bacillus stearothermophilus* (Kubo, M., et. al., (1988) Journal of General Microbiology 134, 1883–1892).

Therefore, in the present specification, the protease coded by this nprM gene or the gene from *Bacillus thermoproteolyticus* is referred to as "wild type thermolysin-like neutral metallo-protease".

Alteration of specific activity and stability of thermolysin-like neutral metallo-protease has very recently been reported (Kubo M., et al., (1992) Applied and Environmental Microbiology, 58, 3779–3783). In this article various mutants have been described which differ in one or more amino acid residues in the primary structure, especially at positions 93, 110, 114, 115, 136, 137, 143, 151, 157, 193, 211, 217 and 221. But in this reference, the activity was measured only by casein digestion method. None of these mutants, however, did show any substantially improved activity in relation to Z-APM synthesis or digestion. It now (as described further in the examples below) also has been established that the activity for casein digestion does not correlate to that for Z-APM synthesis: it appears that even if the specific activity for casein digestion increases, the specific activity for Z-APM synthesis does not always increase.

Based on these observations, and because there are various problems in the enzymatic synthesis of Z-APM, such as relatively low activity of the enzyme, inactivation of the enzyme during the condensation reaction and hydrolysis of the product Z-APM and the starting material L- or D,L-phenylalanine methyl ester (PM), due to the long reaction time, and/or unfavorable pH conditions, there is need to develop improved enzymes that have higher activity for the synthesis of Z-APM than wild-type thermolysin. Of course where PM is mentioned in this application also its salts are included in the meaning of the term PM.

SUMMARY OF THE INVENTION

The object of the invention is to solve such problems as mentioned above. It was found that enzymes having excellent characteristics can be obtained when an appropriate substitute amino acid at certain positions is selected from among various candidates. Thus, from the thermolysin-like neutral metallo-protease having the (wild type) amino acid sequence of SEQ ID NO:i shown below, novel proteases were derived by replacing one or more amino acid residues at certain positions in the sequence with other amino acid residues than the original ones. Specifically, the novel modified proteases according to the invention are obtained therefrom by replacement of at least one of the following amino acid residues with an amino acid different therefrom: 144th (leucine), 150th (aspartic acid), 187th (glutamic acid) and 227th (asparagine) amino acid residues.

(SEQ ID NO: 1)

| Ile 1 | Thr | Gly | Thr | Ser 5 | Thr | Val | Gly | Val | Gly 10 | Arg | Gly | Val | Leu | Gly 15 |
|---|---|---|---|---|---|---|---|---|---|---|---|---|---|---|
| Asp | Gln | Lys | Asn | Ile 20 | Asn | Thr | Thr | Tyr | Ser 25 | Thr | Tyr | Tyr | Tyr | Leu 30 |
| Gln | Asp | Asn | Thr | Arg 35 | Gly | Asn | Gly | Ile | Phe 40 | Thr | Tyr | Asp | Ala | Lys 45 |
| Tyr | Arg | Thr | Thr | Leu 50 | Pro | Gly | Ser | Leu | Trp 55 | Ala | Asp | Ala | Asp | Asn 60 |
| Gln | Phe | Phe | Ala | Ser 65 | Tyr | Asp | Ala | Pro | Ala 70 | Val | Asp | Ala | His | Tyr 75 |
| Tyr | Ala | Gly | Val | Thr 80 | Tyr | Asp | Tyr | Tyr | Lys 85 | Asn | Val | His | Asn | Arg 90 |
| Leu | Ser | Tyr | Asp | Gly 95 | Asn | Asn | Ala | Ala | Ile 100 | Arg | ser | Ser | Val | His 105 |
| Tyr | Ser | Gln | Gly | Tyr 110 | Asn | Asn | Ala | Phe | Trp 115 | Asn | Gly | Ser | Gln | Met 120 |
| Val | Tyr | Gly | Asp | Gly 125 | Asp | Gly | Gln | Thr | Phe 130 | Ile | Pro | Leu | Ser | gly 135 |
| Gly | Ile | Asp | Val | Val 140 | Ala | His | Glu | Leu | Thr 145 | His | Ala | Val | Thr | Asp 150 |
| Tyr | Thr | Ala | Gly | Leu 155 | Ile | Tyr | Gln | Asn | Glu 160 | Ser | Gly | Ala | Ile | Asn 165 |
| Glu | Ala | Ile | Ser | Asp 170 | Ile | Phe | Gly | Thr | Leu 175 | Val | Glu | Phe | Tyr | Ala 180 |

| | | | | | | | | | | | | | | |
|---|---|---|---|---|---|---|---|---|---|---|---|---|---|---|
| Asn | Lys | Asn | Pro | Asp 185 | Trp | Glu | Ile | Gly | Glu 190 | Asp | Val | Tyr | Thr | Pro 195 |
| Gly | Ile | Ser | gly | Asp 200 | Ser | Leu | Arg | ser | Met 205 | Ser | Asp | Pro | Ala | Lys 210 |
| Tyr | Gly | Asp | Pro | Asp 215 | His | Tyr | ser | Lys | Arg 220 | Tyr | Thr | Gly | Thr | Gln 225 |
| Asp | Asn | Gly | Gly | Val 230 | His | Ile | Asn | Ser | Gly 235 | Ile | Ile | Asn | Lys | Ala 240 |
| Ala | Tyr | Leu | Ile | Ser 245 | Gln | gly | Gly | Thr | His 250 | Tyr | Gly | Val | Ser | Val 255 |
| Val | Gly | Ile | Gly | Arg 260 | Asp | Lys | Leu | Gly | Lys 265 | Ile | Phe | Tyr | Arg | Ala 270 |
| Leu | Thr | Gln | Tyr | Leu 275 | Thr | Pro | Thr | Ser | Asn 280 | Phe | Ser | Gln | Leu | Arg 285 |
| Ala | Ala | Ala | Val | Gln 290 | Ser | ala | Thr | Asp | Leu 295 | Tyr | Gly | Ser | Thr | Ser 300 |
| Gln | Glu | Val | ala | Ser 305 | Val | Lys | Gln | ala | Phe 310 | Asp | Ala | Val | Gly | Val 315 |
| Lys | | | | | | | | | | | | | | |

In particular, the modified enzymes having the amino acid sequence as shown above, but with modification(s) of at least one of the amino acid residues at positions 144th, 150th, 187th and 227th, exhibit the higher specific activity for synthesis or digestion of Z-APM than the wild type enzyme. It solves the problems of how to enhance the activity of Z-APM synthesis of the thermolysin-like neutral metallo-protease derived from *Bacillus stearothermophilus*. Moreover, enzymes are provided which have higher activity at lower pH, and therefore ensure that during the synthesis of Z-APM less hydrolysis of Z-APM and PM occurs.

It is to be noted that those enzymes which are obtained by replacement at two or more of the positions specified above, naturally fall within the scope of the present invention. The same is true for those enzymes which are obtained by replacement of at least one of the amino acid residues specified above and by additional replacement of at least one of the other amino acid residues with an amino acid different therefrom.

DETAILED DESCRIPTION OF THE INVENTION

Novel proteases described in this invention are derivatives having a modified sequence different from that of the wild type thermolysin-like neutral metallo-protease. In particular, the novel proteases have an enhanced activity for Z-APM synthesis and digestion. Typically, this is determined by analyzing the activity for Z-APM synthesis and/or digestion, and comparing these activities with that of wild type thermolysin-like neutral metallo-protease assayed in the same manner. This procedure is described further in the examples.

Modified enzymes can be produced by methods known per se to those skilled in the art.

The preferred method for producing the modified proteases of this invention is to introduce an amino acid sequence variation into predetermined positions of at least one of the 144th, 150th, 187th and 227th positions of the thermolysin-like neutral metallo-protease by recombinant DNA methods. The suitability of the proteases obtained can be determined by assay tests for the ultimate applications. Various methods are known which can be used to introduce mutations into cloned DNAs. For example, mutant nprM gene fragments are prepared by using the M13 phage mutagenesis method (Vandeyar, M., et al., (1988) Gene, 65, 129).

The plasmid and phage DNAs used for templates in this method, can be derived from the known plasmid pMK1 (Kubo, M. and Imanaka, T., (1989) J. Bacteriol, 171, 4080–4082). Several restriction endonucleases are used for digestion and cloning of the fragments of nprM gene into another plasmid or into phage vectors. The mutagenic primers should be complementary to the single-stranded template DNA containing the nprM gene, except for the codon(s) for the replaced amino acid residue(s). Various nucleotide sequences are conceivable for that purpose. By using these mutagenic primers which have (a) different codon(s) for the replaced amino acid residue(s), any desired amino acid replacement can be attained.

Alternatively, the nprM gene can be mutated by the PCR technique (polymerase chain reaction) using chemically synthesized primers (Higuchi, R., Krummel, B., and Saiki, R. K., (1988) Nucleic Acids Res. 16, 7351–7367). When a restriction enzyme site exists in the vicinity of the site of mutation, this PCR method is particularly useful. Since, for example, there is a cleavage site for the restriction enzyme SphI in the vicinity of the codon for aspartic acid in the 150th position of the wild type thermolysin-like metalloprotease, mutagenic primers containing this SphI site can be used for producing mutants in the 150th position. The mutagenic primer thus is used as a sense primer. As the reverse-direction primer (antisense), an oligonucleotide can be used, which is complementary to the nprM gene downstream from, for example, the AatI cleavage site of the nprM gene.

Two methods can be used for effecting mutagenesis at more than one site. One method comprises effecting simultaneous mutagenesis at all the target sites, while the other comprises introduction of mutations one after the other. Both methods actually give plasmids with mutations at more than one site.

A general method for recombinant thermolysin-like neutral metallo-protease preparation is described in the literature (Kubo, M. and Imanaka, T., (1989) J. Bacteriol., 171, 4080–4082) and comprises: insertion of the DNA encoding the modified thermolysin-like neutral metallo-protease into an expression vector, using this vector to transform a host cell, culturing the transformant until the modified metalloprotease accumulates in the culture and the then recovering modified enzyme from the culture. However, the plasmid pMK1 used in this reference is more than 20 kb in size and therefore it is substantially difficult to transform *Escherichia coli* with said plasmid. Furthermore, it was found that, in *Bacillus subtilis* too, the plasmid pMK1 drops out to a considerable extent in the latter stage of cultivation.

Therefore, to overcome such problems the inventors constructed shuttle vectors with which both hosts, *Escherichia coli* and *Bacillus subtilis* can be transformed and which can express the nprM gene in these hosts. As shown in FIG. 1 to FIG. 4, two shuttle vectors containing the nprM gene have been thus constructed (pUBTZ1 and pUBTZ2). When these are used to transform such strains of *Escherichia coli* as HB101 and JM103, the nprM gene is expressed in those strains. In addition, transformation of such *Bacillus subtilis* strains as DB104, DB117 and MT-2 with these plasmids led to successful expression of the nprM gene. Also no drop-out is observed in the latter stage of cultivation.

Similar results and advantages of using these shuttle vectors are obtained by using the modified thermolysin-like neutral metallo-protease genes instead of the wild type gene.

The modified thermolysin-like neutral metallo-protease can be produced in recombinant bacteria and is secreted in culture media. These proteases are recovered by ammonium sulfate precipitation and purified to homogeneity in the conventional manner, for example by hydrophobic interaction chromatography and/or gel filtration.

The modified proteases are used to synthesize Z-APM, which is a precursor of aspartame, more effectively than wild type thermolysin-like neutral metallo-protease. This is indicated by comparing the activities for the Z-APM digestion and Z-APM synthesis of these modified proteases to those of the wild-type enzyme. These are to be found extremely higher than those of the wild type enzyme. The measured values of these activities will be described in the following examples.

In this invention, the positions of the 144th, 150th, 187th and 227th from the amino-terminal amino acid in the thermolysin-like neutral metallo-protease have been found to have a great effect for enhancing the activity for Z-APM digestion and synthesis, especially when two or three of these sites were combined.

It is to be noted that the activity of casein digestion is not related to the activity of Z-APM synthesis or digestion. When the activities of mutant enzymes for casein and Z-APM are compared, it is clear that even if the activity for casein digestion is decreased, the activity for Z-APM synthesis and/or digestion can greatly be enhanced. The following examples are given only for illustrating the present invention and are by no means limitative of the scope of the invention.

EXAMPLE 1

(Synthesis of the mutant thermolysin-like neutral metalloprotease which has the mutation at the 187th (Example 1A) or 227th (Example 1B) amino acid residue.)

1 µg of the plasmid pMK1 containing the thermolysin-like neutral metallo-protease gene nprM derived from *Bacillus stearothermophilus* MK232 was digested with 5 units of each of PstI and BamHI in 20 µl of a reaction mixture (50 mM Trishydrochloride at pH 7.5, 10 mM MgCl₂, 1 mM DTT) at 37° C. for 2 hours. The sample was subjected to 1% agarose gel electrophoresis, and an approximately 3.5 kb DNA fragment was separated and purified using a Bio-101 Gene Clean DNA purification kit.

Separately, 1 µg of the plasmid pUC9 was treated with 5 units of each of PstI and BamHI in 20 µl of the same reaction mixture as mentioned above at 37° C. for 2 hours.

Figure 5:
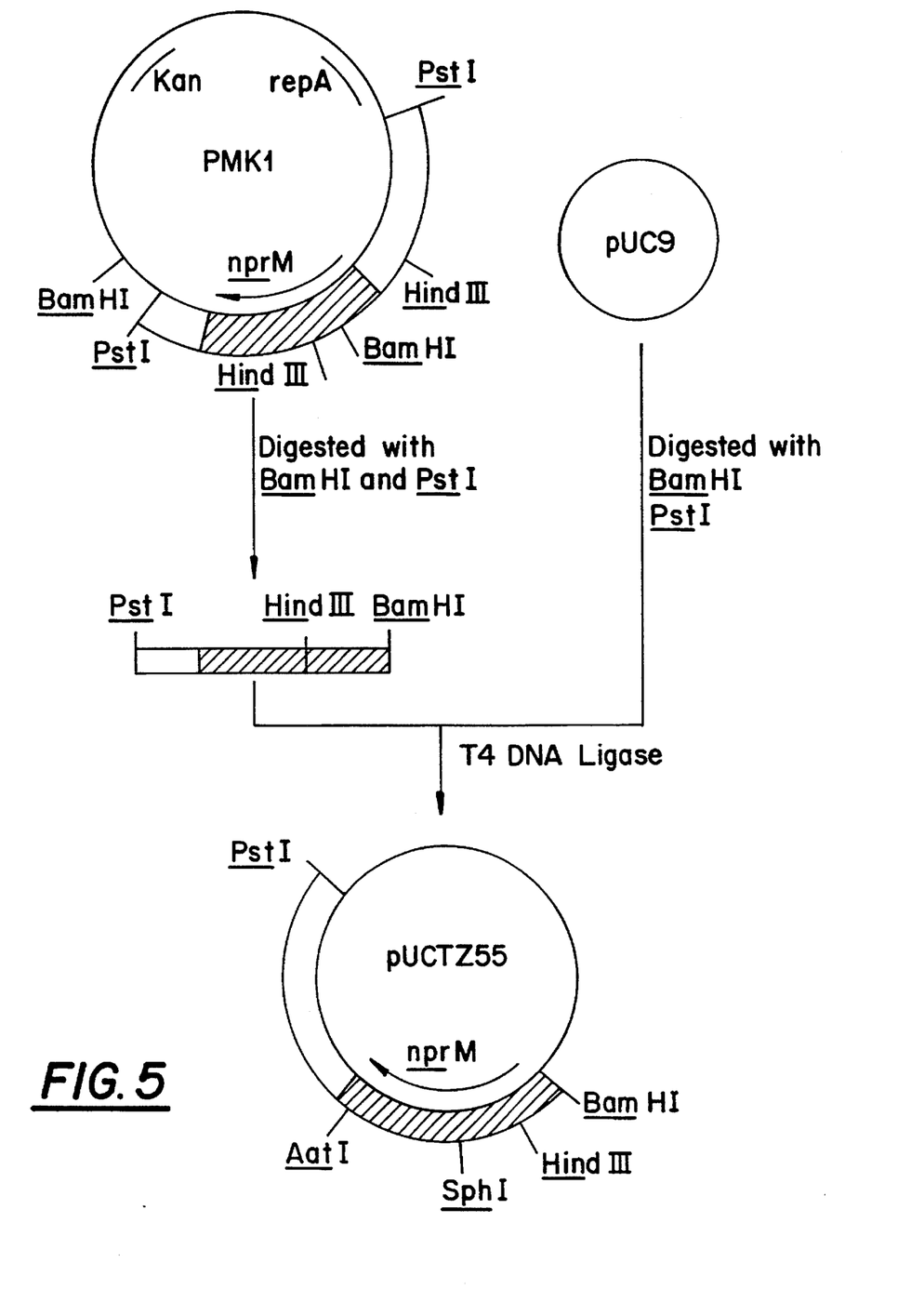
FIG. 5 shows the scheme used for constructing a recombinant plasmid named pUCTZ55 from the known plasmid pMK1.

The PstI-BamHI fragment of the nprM gene was ligated with the PstI-BamHI digest of pUC9 using a Takara Shuzo DNA ligation kit. The ligation mixture was used to transform *Escherichia coli* JM109 in a conventional method to give a recombinant plasmid (pUCTZ55) containing the PstI-BamHI fragment of the nprM gene (FIG. 5).

1 µg of the recombinant plasmid pUCTZ55 was digested with 5 units of each of SphI and BclI in 20 µl of a reaction mixture (50 mM Tris-hydrochloride at pH 7.5, 10 mM MgCl₂, 100 mM NaCl, 1 mM DTT) at 37° C. for 2 hours. The sample was subjected to 1% agarose gel electrophoresis and an approximately 550 kbp DNA fragment was separated and purified using a Bio-101 Gene Clean DNA purification kit.

Separately, 1 µg of the phage vector M13mp18 was digested with 5 units of each of SphI and BamHI in 20 µl of the same reaction mixture as mentioned above at 37° C. for 2 hours.

Figure 6:
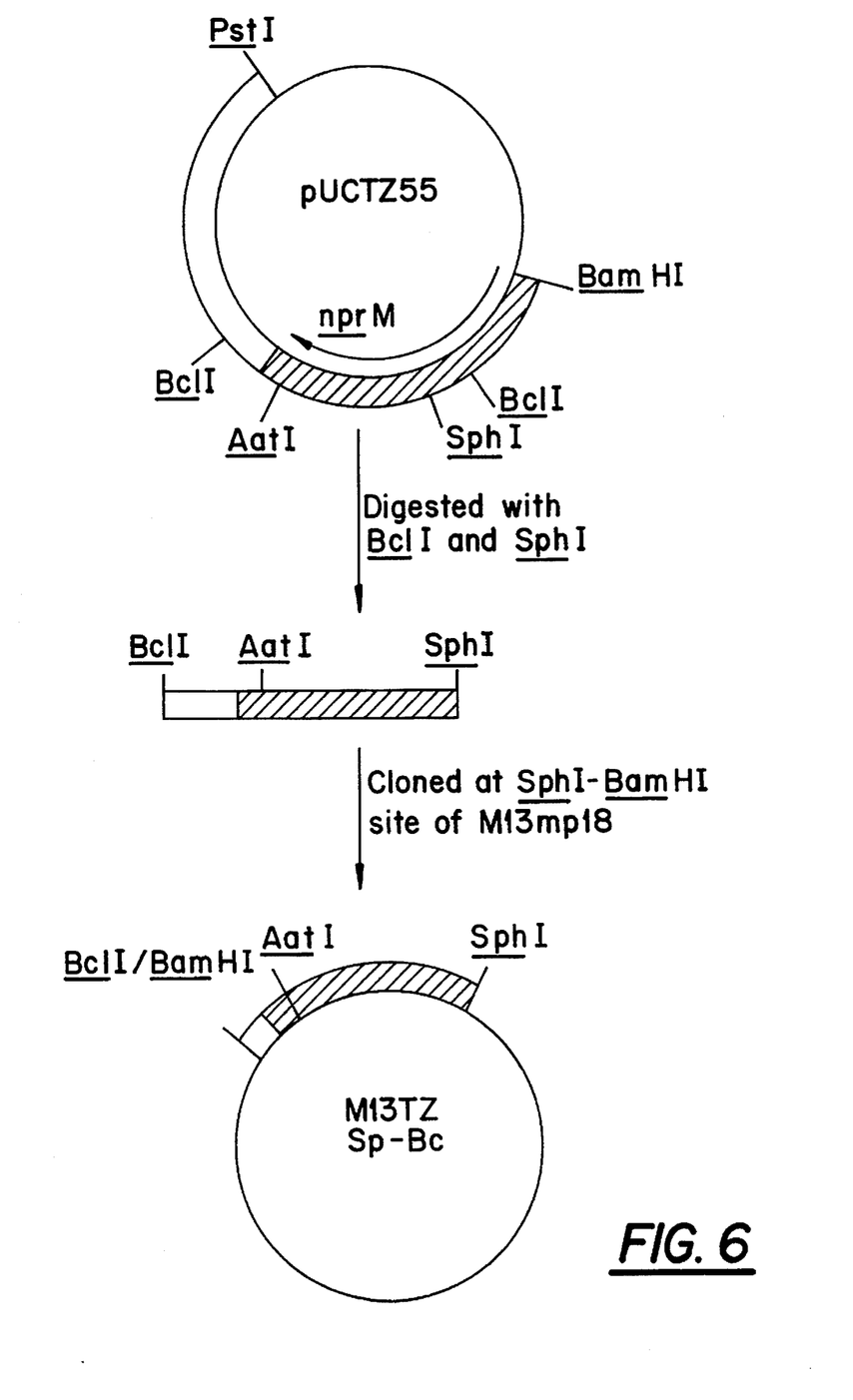
FIG. 6 shows the scheme used for constructing a recombinant M13 phage named M13TZSp-Bc from the plasmid pUCTZ55.

The SphI-BclI fragment of the nprM gene was ligated with the SphI-BamHI digest of M13mp18 using a Takara Shuzo DNA ligation kit. The ligation mixture was used to transform *Escherichia coli* JM109 in a conventional method to give a recombinant phage (M13TZSp-Bc) containing the SphI-BclI fragment of the nprM gene (FIG. 6).

The single stranded DNA was prepared from the M13TZSp-Bc by a conventional method and subjected to mutagenesis. The oligonucleotides used for mutagenesis were prepared using an Applied Biosystems model 380B DNA synthesizer.

The mutagenic oligonucleotides used for the replacement of the 187th residue (glutamic acid to glutamine) (Example 1A) and the 227th residue (asparagine to histidine) (Example 1B) are shown below.

The mutageneses were performed using a USB T7-GEN in vitro mutagenesis kit, followed by DNA sequencing for confirmation of the mutation.

The double-stranded DNA of the mutated M13TZSp-Bc was prepared by a conventional method and 1 µg of the double-stranded DNA was digested with 5 units of each of SphI and AatI in 20 µl of reaction mixture (50 mM Trishydrochloride at pH 7.5, 10 mM MgCl₂, 100 mM NaCl, 1 mM DTT) at 37° C. for 2 hours, and each sample was electrophoresed on a 1% agarose gel. A DNA fragment of about 550 kb was isolated from each of the M13TZSp-Bc digests and the DNA fragments were purified using a Bio-101 Gene Clean DNA purification kit.

Figure 1:
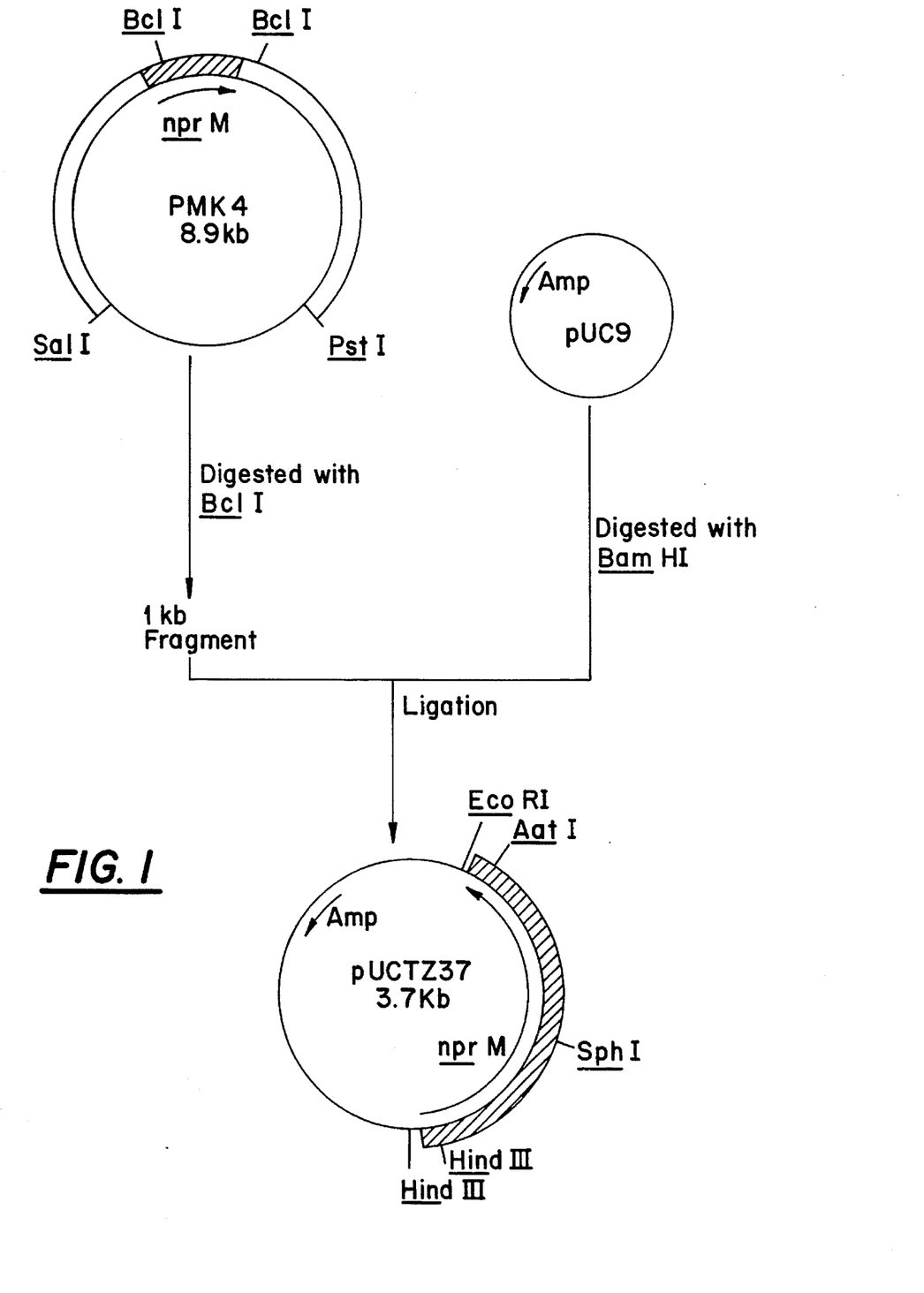
FIG. 1 shows the scheme used for constructing a recombinant plasmid named pUCTZ37 from the known plasmid pMK4.

Simultaneously, a vector fragment for the expression in *Bacillus subtilis* was produced by the method as described below. From a plasmid pMK4 (Yamada et al., (1991) Gene, 99, 109–114), the about 1.0 kb DNA fragment containing part of the nprM gene was digested with BclI and was cloned in BamHI site of a plasmid pUC9 to construct a plasmid pUCTZ37 (FIG. 1).

Figure 2:
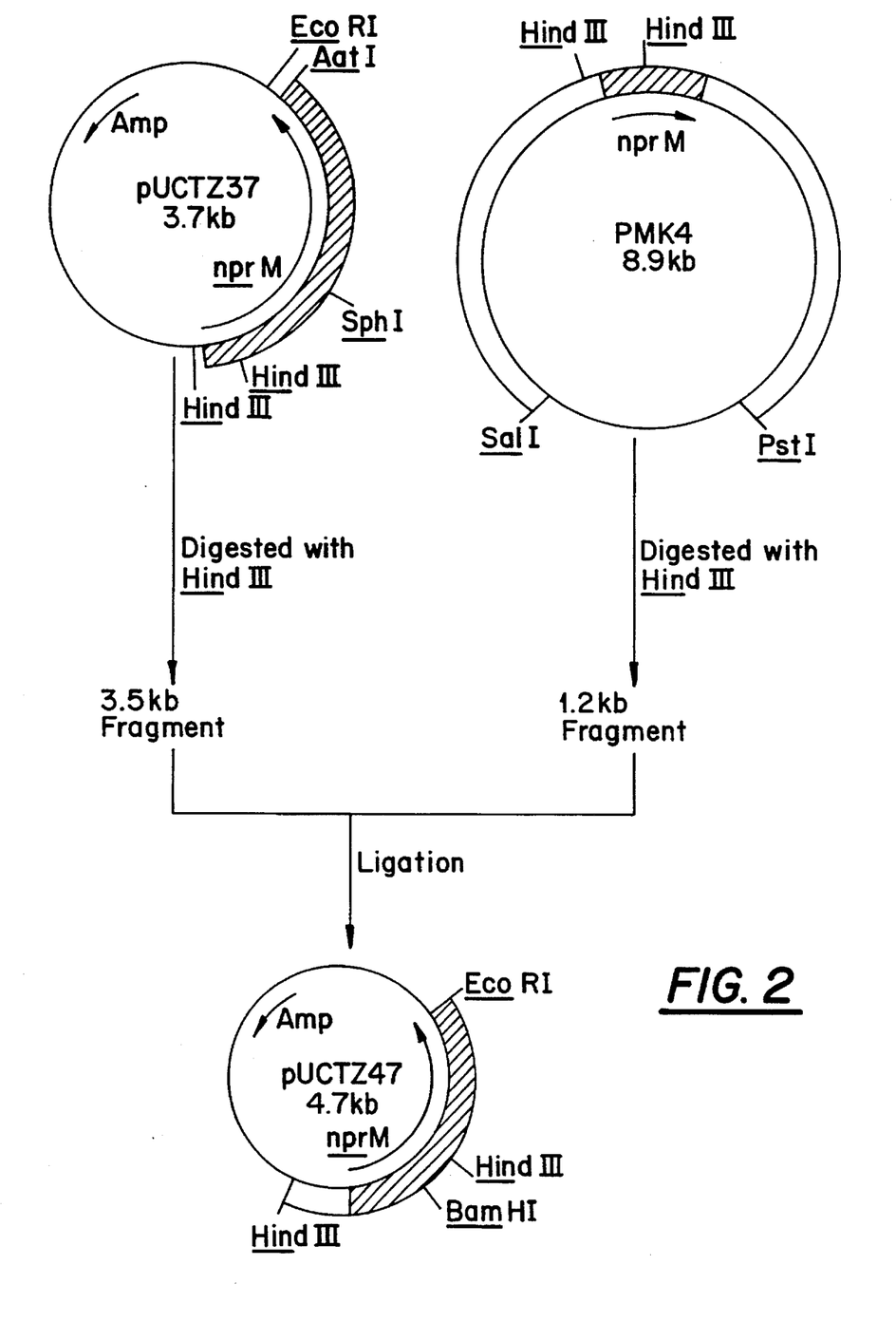
FIG. 2 shows the scheme used for constructing a recombinant plasmid named pUCTZ47 from the plasmid pMK4 and the plasmid pUCTZ37.

The plasmid pUCTZ37 was an incomplete one not having the 5'-terminal region of nprM gene. The plasmid pUCTZ37 was digested with restriction endonuclease HindIII and the about 1.2 kb HindIII fragment of pMK4 was cloned into the larger pUCTZ37 fragment to construct plasmid pUCTZ47 (FIG. 2). The recombinant plasmid pUCTZ47 contains the full length sequence of nprM and its transcriptional promotor sequence.

Figure 3:
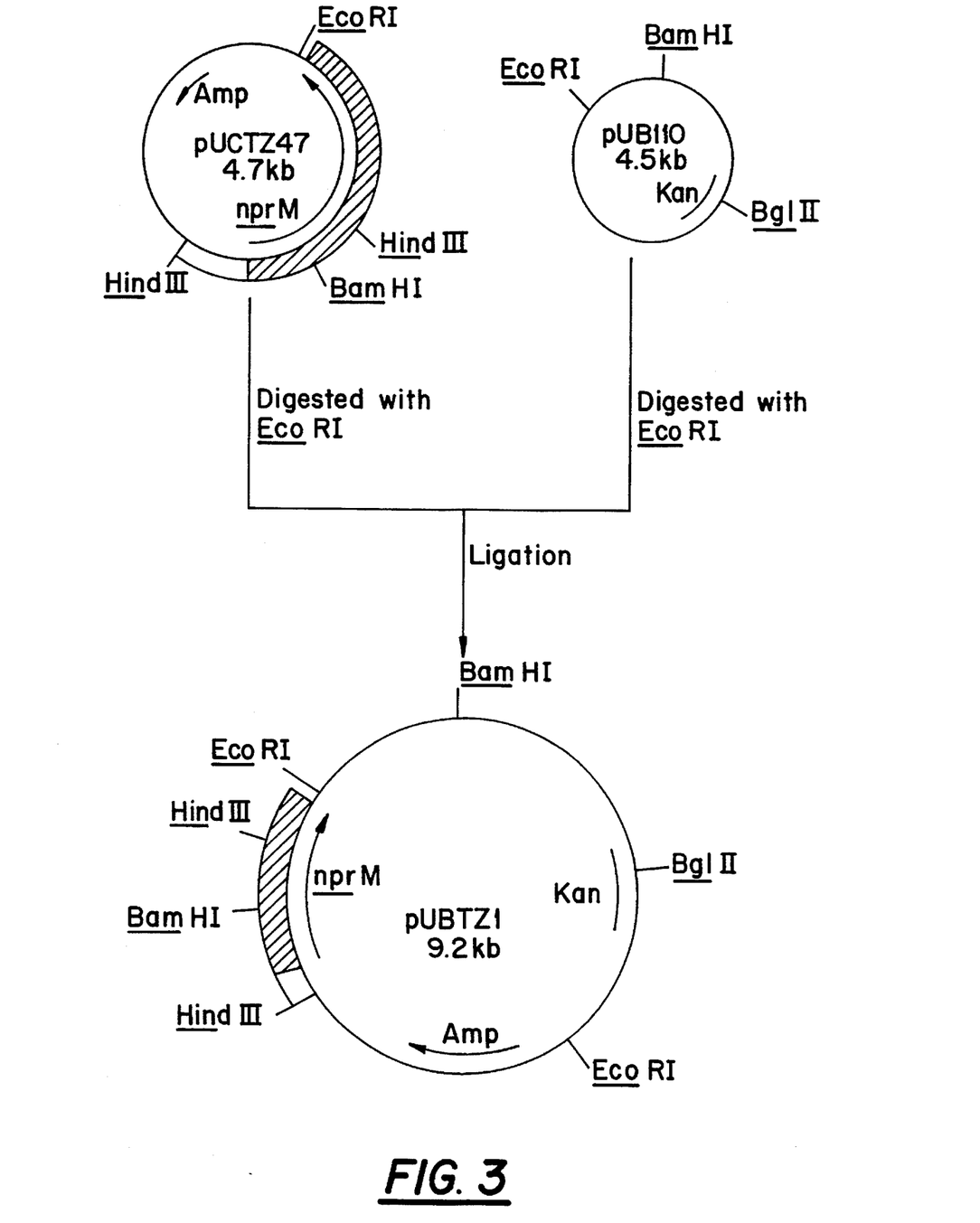
FIG. 3 shows the scheme used for constructing a recombinant plasmid named pUBTZ1 from the known plasmid pUCTZ47 and the plasmid pUB110.

To construct shuttle vectors between *Escherichia coli* and *Bacillus subtilis*, both pUCTZ47 and pUB110 (Lacey et al., 1974) were digested with EcoRI and ligated with T4 polynucleotide kinase to construct plasmid pUBTZ1, as shown in FIG. 3.

Figure 4:
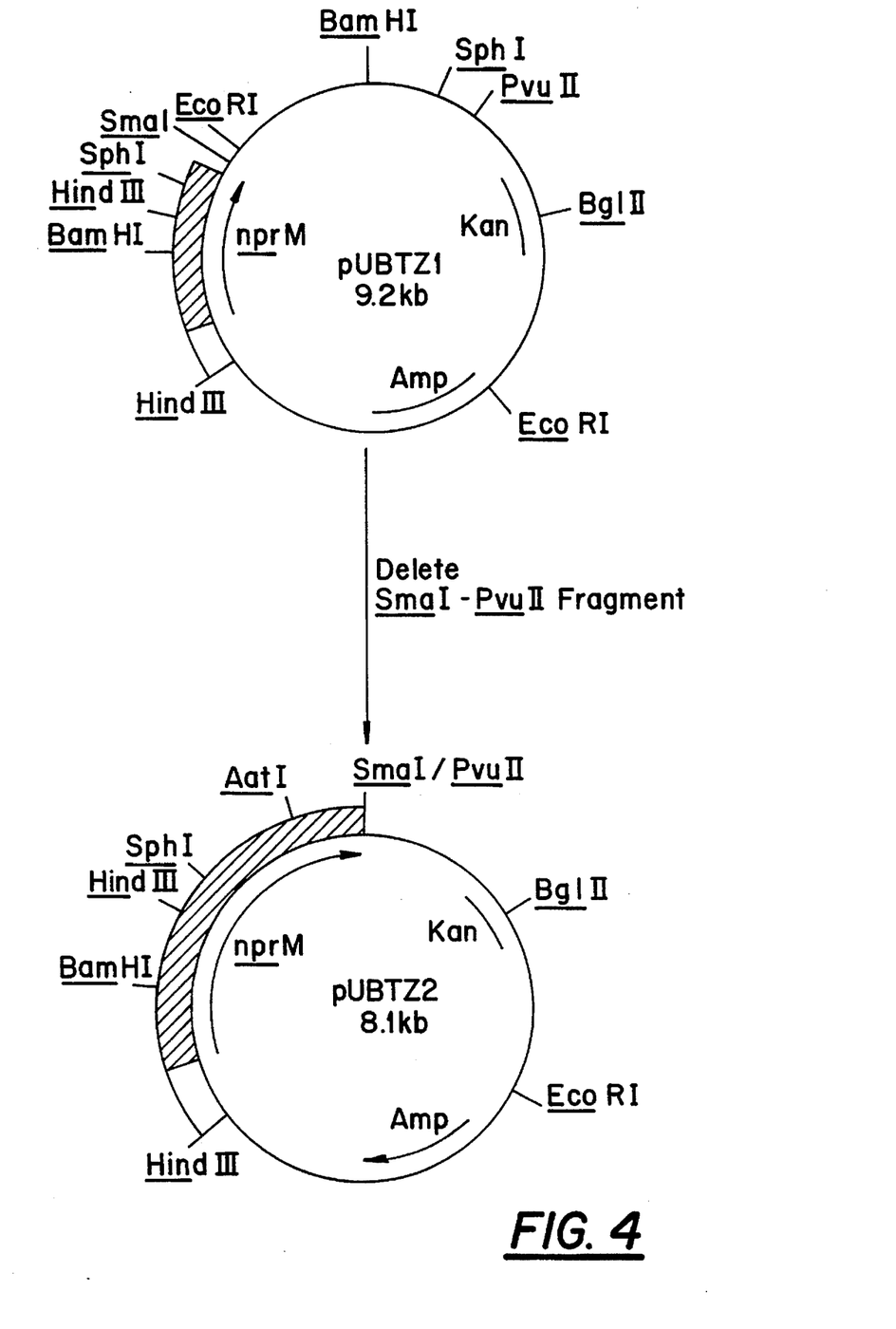
FIG. 4 shows the scheme used for constructing a plasmid named pUBTZ2 from the plasmid pUBTZ1.

Finally, the DNA fragment between the restriction site by endonuclease SmaI and PvuII was deleted from the plasmid pUBTZ1 as shown in FIG. 4, to construct plasmid pUBTZ2. Plasmid pUBTZ2 has single BamHI, SphI and AatI restriction sites in the nprM gene. The replacement of the wild type gene with the mutant gene was carried out as described below.

Figure 7:
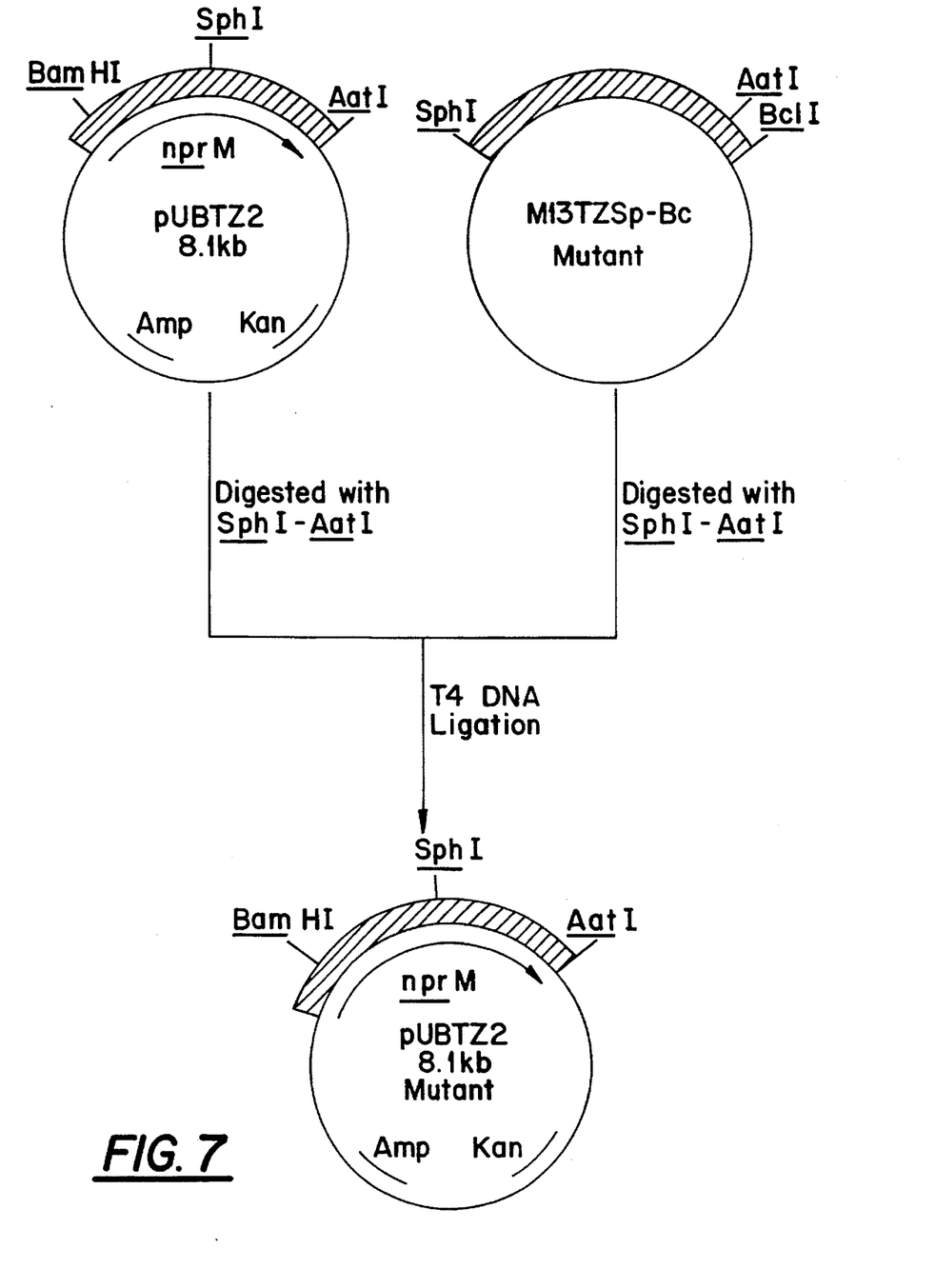
FIG. 7 shows the scheme used for constructing a plasmid pUBTZ2 (mutant) from the plasmid pUBTZ2 and M13TZSp-Bc (mutant).

The plasmid pUBTZ2 was digested with SphI and AatI, and a 7.6 kb fragment was isolated. The mutated SphI-AatI fragments of the nprM gene (about 550 bp) were ligated with the thus-obtained pUBTZ2 SphI-AatI fragment using a Takara Shuzo DNA ligation kit. The ligation mixture was used to transform *Escherichia coli* JM103 in a conventional manner to give recombinant plasmids pUBTZ2 (E187Q) and pUBTZ2 (N227H) (FIG. 7).

The recombinant plasmid pUBTZ2 (mutant) was transformed to *Bacillus subtilis* strain MT-2 by a conventional method. The cell suspension was spread on an LB agar plate containing 1% casein and 5 µg/ml kanamycin and incubated at 37° C. overnight. Finally the recombinant plasmid pUBTZ2 (mutant) was obtained by isolation of halo-forming colonies.

A single colony of the recombinant *Bacillus subtilis* MT-2/pUBTZ2 (mutant) was transferred to 5 ml of LB medium containing kanamycin (5 µg/ml) and incubated at 37° C. overnight. The culture was transferred to 500 ml of 2L medium (2% Bacto tryptone, 1% yeast extract, 0.5% NaCl) containing kanamycin (5 µg/ml) and incubated at 37° C. for 20 hours. The culture broth was centrifuged at 8,000 rpm for 30 minutes to remove bacteria, ammonium sulfate was added to the supernatant to attain 60% saturation and the mixture was stirred overnight at 4° C.

The precipitate was recovered by centrifugation and dissolved in 10 ml of Buffer A (20 mM Tris-hydrochloride at pH 9.0, 10 mM $CaCl_2$). The solution was applied to 20 ml of Butyl-Toyopearl, followed by an elution with Buffer A at a flow rate of 1.5 ml/minute. Active fractions were combined and subjected to salting out with 60% saturated ammonium sulfate. The precipitate was collected by centrifugation at 15,000 rpm. for 30 minutes, and dissolved in 5 ml of Buffer B (20 mM Tris-hydrochloride at pH 7.5, 10 mM $CaCl_2$). The enzyme solution was further applied to a gel-filtration column (TSK Gel G2000 SW 21.5×600 mm), followed by elution with Buffer B at a flow rate of 1 ml/minute. Active eluate fractions were combined to give the purified enzyme.

EXAMPLE 2

(Synthesis of the mutant thermolysin-like neutral metalloprotease which has the mutation at the 144th amino acid residue by random mutagenesis.)

Figure 8:
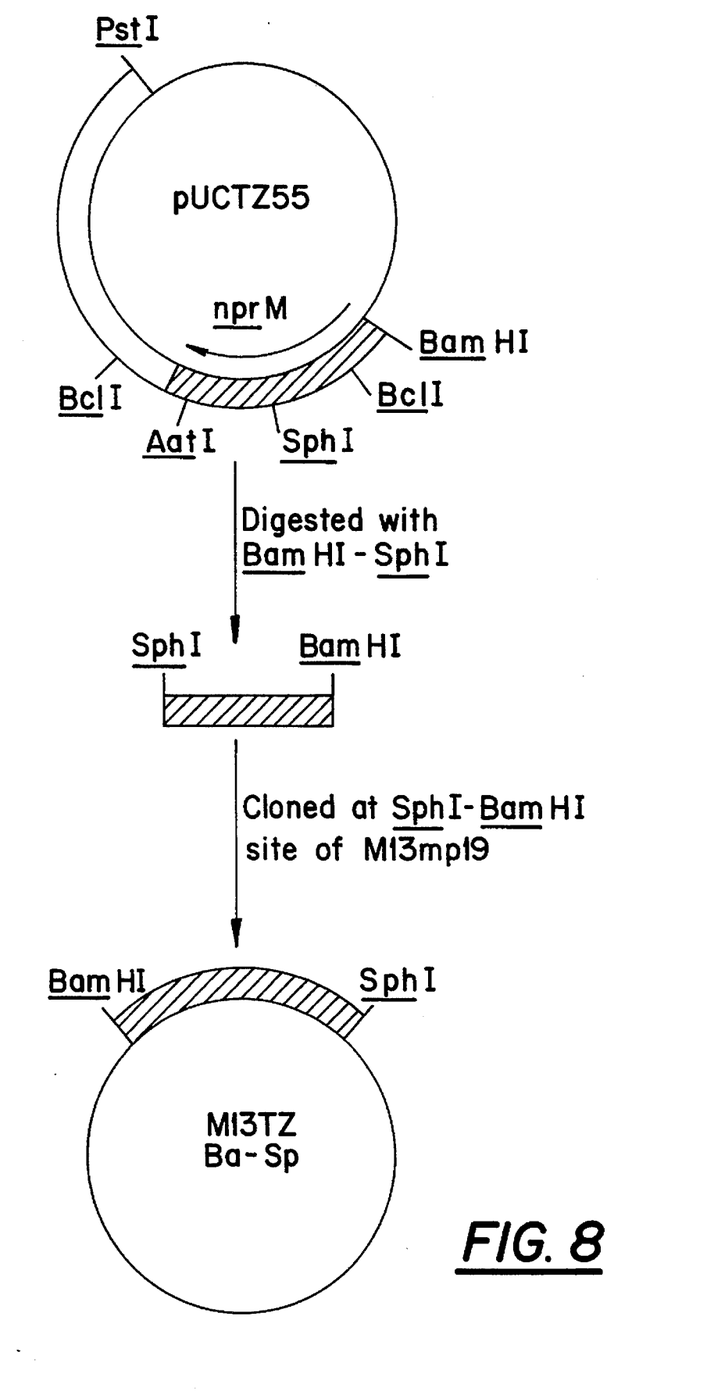
FIG. 8 shows the scheme used for constructing a recombinant M13 phage named M13TZBa-Sp from the plasmid pUCTZ55.

A recombinant phage M13TZBa-Sp containing the BamHI-SphI fragment of the nprM gene was obtained in the same way as described in example 1, except for the restriction enzymes (BamHI and SphI instead of PstI and BamHI) and the M13 phage vector (mp19 instead of mp18) used. The procedure for the production of the recombinant phage M13TZBa-Sp is shown in FIG. 8.

The single-stranded DNA of M13TZBa-Sp was incubated at 21.5° C. for 4.5 hours in 20 µl of a 0.25M sodium acetate buffer containing 1M sodium nitrite (pH 4.3), and the DNA was recovered by ethanol precipitation.

The recovered DNA was dissolved in the reaction mixture for PCR (67 mM Tris-hydrochloride pH 8.8, 16.6 mM ammonium sulfate, 6.7 mM $MgCl_2$, 10 mM 2-mercaptoethanol, 0.2 mM dATP, 0.2 mM dTTP, 0.2 mM dGTP, 0.2 mM dCTP, 1 µM M13 forward universal primer, 1 µM M13 reverse primer), and 1 unit of Tth DNA polymerase was added. The solution was covered with one drop of mineral oil. The denaturation at 93° C. for 1 minute, the annealing at 45° C. for 1 minute and the extension at 72° C. for 45 seconds were repeated 30 times. After the reaction, the water layer was recovered, extracted with phenol and treated with ethanol to recover the amplified DNA by precipitation.

Half of the quantity of the DNA was digested with 5 units of each of BamHI and SphI at 37° C. for 2 hours in 20 µl of a reaction mixture (50 mM Tris-hydrochloride at pH 7.5, 10 mM $MgCl_2$, 100 mM NaCl, 1 mM DTT). Then the reaction mixture was incubated at 70° C. for 5 minutes. The mutated BamHI-SphI fragment was ligated with the BamHI-SphI fragment of pUBTZ2 (7.4 kb) using a Takara Shuzo DNA ligation kit. The ligation mixture was used to transform *Escherichia coli* JM103 in a conventional method to give transformant JM103/pUBTZ2 (mutant).

3 ml of an alkaline solution (0.2N NaOH, 0.2% SDS) was added to an agar plate containing the transformant colonies to dissolve the colonies and 1 ml of solution was recovered. 1 ml of 5M potassium acetate was added to the solution, and the mixture was centrifuged for 20 minutes to remove the precipitate after keeping on ice for 10 minutes. The supernatant was treated with phenol and precipitation was achieved by treatment with ethanol. The precipitate was dissolved after drying in vacuum and used as a mutant library.

The *Bacillus subtilis* strain MT-2 was transformed by the mutant library in a conventional method. The cell suspension was spread on an LB agar plate containing 1% casein and 5 µg/ml kanamycin and incubated overnight at 37° C. and finally 140 halo-forming colonies were isolated.

The single colonies were transferred to 3 ml of LB medium containing 5 µg/ml kanamycin and incubated at 37° C. overnight. The culture was centrifuged for 5 minutes at 10,000 rpm. and 0.3 ml of saturated solution of ammonium sulfate and 0.04 ml of butyl-toyopearl 650S was added to 1.2 ml of the supernatant. The mixture was stirred and was kept at room temperature for 5 minutes. Then, the solution was centrifuged at 10,000 rpm for 1 minute to remove the supernatant and the precipitate was suspended in washing solution (8 mM Tris-hydrochloride at pH 8.0, 8 mM calcium chloride, 20% saturated ammonium sulfate) and was packed in a small diameter pipette-type column. After washing with 0.6 ml of washing solution, the enzyme was eluted by using 0.2 ml of eluent (10 mM Tris-hydrochloride at pH 8.0, 10 mM calcium chloride). The enzyme solution was desalted by using gel filtration (Sephadex PD10) and finally 0.5 ml of the purified enzyme solution was obtained.

The concentration of the enzyme was determined by the dye-binding assay (Bradford, M. M., (1976) Anal. Biochem., 72, 248–254) and Z-APM digestion activity was measured for screening of mutated enzymes in the following way.

1 ml of a substrate solution (10mM Tris-maleate at pH 8.0, 10 mM calcium chloride, 10 mM Z-APM) was mixed with 0.05 ml of the enzyme solution and was incubated at 37° C. for 20 minutes. Then 0.5 ml of stop solution (0.1M acetic acid) was added, followed by further addition of 1 ml of ninhydrin solution. After 15 minutes of incubation at 100° C., 2 ml of 50% ethanol was added and the absorbance was measured at 570 nm. The specific activity defined as the change in absorbance per mg of enzyme protein was expressed in terms of a relative value compared to that of the wild type enzyme. Two clones having higher activity for Z-APM digestion were obtained.

| Enzyme | Z-APM digestion activity (%) |
| --- | --- |
| Wild type | 100 |
| Clone 1 | 260 |
| Clone 2 | 280 |

It should be noted that these activity values were determined by rough method.

The plasmid DNA was extracted from these two clones and the nucleotide sequences of these clones were determined. It was found from the nucleotide sequences that the two clones were identical, and that the 38th glycine residue and the 144th leucine residue had been replaced by glutamine and serine respectively. The clone is represented as G38Q-L144S hereafter.

1 μg of each of the plasmid pUBTZ2 (G38Q-L144S) and pUI3TZ2 (wild type) were incubated in 20 μl of a reaction mixture (50 mM Tris-hydrochloride at pH 7.5, 10 mM magnesium chloride, 50 mM sodium chloride, 1 mM DTT) containing 5 units of HindIII at 37° C. for 2 hours. These samples were electrophoresed on an 1% agarose gel to isolate an about 1.1 kb DNA fragment and an about 7 kb DNA fragment respectively, and both fragments were purified using BIO-101 Gene Clean DNA purification kit.

The DNA fragment of about 7 kb derived from pUBTZ2 (G38Q-L144S) and the DNA fragment of about 1.1 kb derived from pUBTZ2(wild type) were ligated using Takara Shuzo DNA ligation kit. Each ligation mixture was used to transform *Escherichia coli* JM103 in a conventional method. The transformants were screened by rapid DNA isolation and DNA sequencing to isolate the clone of pUBTZ2 (L144S).

Each single colony of each transformant *Bacillus subtilis* MT-2/pUBTZ2 (G38Q-L144S) and MT-2/pUBTZ2 (L144S) was transferred to 5 ml of LB medium containing kanamycin (5 μg/ml) at 37° C. overnight. The culture was transferred to 500 ml of 2L medium (2% Bacto tryptone, 1% yeast extract, 0.5% NaCl) containing kanamycin (5 μg/ml) and incubated at 37° C. for 20 hours. The culture broth was centrifuged at 8,000 rpm for 30 minutes to remove bacteria, ammonium sulfate was added to the supernatant to attain 60% saturation and the mixture was stirred overnight at 4° C.

The precipitate was recovered by centrifugation and dissolved in 10 ml of Buffer A (20 mM Tris-hydrochloride at pH 9.0, 10 mM CaCl$_2$). The solution was applied to 20 ml of Butyl-Toyopearl, followed by an elution with Buffer A at a flow rate of 1.5 ml/minute. Active fractions were combined and subjected to salting out with 60% saturated ammonium sulfate. The precipitate was collected by centrifugation at 15,000 rpm for 30 minutes, and dissolved in 5 ml of Buffer B (20mM Tris-hydrochloride at pH 7.5, 10 mM CaCl$_2$). The enzyme solution was further applied to a gel-filtration column (TSK Gel G2000 SW 21.5×300 mm), followed by elution with Buffer B at a flow rate of 1 ml/minute. Active fractions were combined to give each purified enzyme.

EXAMPLE 3

(Synthesis of the mutant thermolysin-like neutral metalloprotease which has the mutation at the 150th amino acid residue)

The oligonucleotides used for the mutagenesis were synthesized by using an DNA synthesizer Model 380B produced by Applied Biosystems Co. LTD. The nucleotide sequences of the mutagenesis primers were

```
              (SEQ ID NO: 4)
5' -AACGCATGCGGTAACCAATTATACAGC- 3'
        SphI        Asn
                    150

(SEQ ID NO: 5)
5' -AACGCATGCGGTAACCCATTATACAGC- 3'
        SphI        His (SEQ ID NO: 6)
5' -AACGCATGCGGTAACCAAATATACAGC- 3'
        SphI        Lys
```

Furthermore, a reverse-direction primer was synthesized having the nucleotide sequence described below. (SEQ ID NO:7)

5'-GAGATACCACTTTATTTCACCCCA-3'

1 ng of plasmid pUBTZ2 was dissolved in 100 μl of the reaction mixture for PCR (67 mM Tris-hydrochloride (pH 8.8), 16.6 mM ammonium sulfate, 6.7 mM MgCl$_2$, 10 mM 2-mercaptoethanol, 0.05 mM dATP, 0.05 mM dTTP, 0.05 mM dGTP, 0.05mM dCTP, 1 μM mutagenesis primer, 1 μM reverse-direction primer), and 1 unit of Tth DNA polymerase was added. The solution was covered with one drop of mineral oil. The denaturation at 93° C. for 1 minute, the annealing at 45° C. for 1 minute and the extension at 72° C. for 45 seconds were repeated 30 times. After the reaction, the water layer was recovered, extracted with phenol and treated with ethanol to recover the amplified DNA.

20 μl of a reaction mixture (50 mM Tris-hydrochloride at pH 7.5, 10 mM MgCl$_2$, 100 mM NaCl, 1 mM DTT) containing half amount of the DNA was digested with 5 units each of SphI and AatI at 37° C. for 2 hours, and was incubated at 70° C. for 5 minutes. The mutated SphI-AatI fragment was ligated with SphI-AatI fragment of pUBTZ2 (7.6 kb) using a Takara Shuzo DNA ligation kit. The ligation mixture was used to transform *Escherichia coli* JM103 in a conventional method to give a transformant JM103/ pUBTZ2 (mutant). The substituted amino acid was confirmed by the determination of the nucleotide sequence of these plasmid.

A single colony of the transformant *Bacillus subtilis* MT-2/pUBTZ2(mutant) was transferred to 5 ml of LB medium containing kanamycin (5 μg/ml) at 37° C. overnight. The culture was transferred to 500 ml of 2L medium (2% Bacto tryptone, 1% yeast extract, 0.5% NaCl) containing kanamycin (5 μg/ml) and incubated at 37° C. for 20 hours. The culture broth was centrifuged at 8,000 rpm for 30 minutes to remove bacteria, ammonium sulfate was added to the supernatant to attain 60% saturation and the mixture was stirred overnight at 4° C.

The precipitate was recovered by centrifugation and dissolved in 10 ml of Buffer A (20 mM Tris-hydrochloride at pH 9.0, 10 mM CaCl$_2$). The solution was applied to 20 ml of Butyl-Toyopearl, followed by an elution with Buffer A at a flow rate of 1.5 ml/minute. Active fractions were combined and subjected to salting out with 60% saturated ammonium sulfate. The precipitate was collected by centrifugation at 15,000 rpm for 30 minutes, and dissolved in 5 ml of Buffer B (20 mM Tris-hydrochloride at pH 7.5, 10 mM CaCl$_2$). The enzyme solution was further applied to a gel-filtration column (TSK Gel G2000 SW 21.5×600 mm), followed by elution with Buffer B at a flow rate of 1 ml/minute. Active fractions were combined to give each purified enzyme.

EXAMPLE 4

(Synthesis of a mutant thermolysin-like neutral metallo-protease which has mutations at the 144th, 150th and th amino acid residues)

A three-site mutants of thermolysin-like neutral metallo-protease was constructed as follows. The plasmid pUBTZ2 (N227H), which represents the plasmid containing the mutation at the codon of the 227th amino acid residue from asparagine to histidine, was used as a template for polymerase chain reaction. The mutagenesis primers and the reversdirection primer were the same as those described in Example 3.

The mutagenesis primers:

(SEQ ID NO: 4)

(Example 4A)
5'-AACGCATGCGGTAACCAATTATACAGC-3' (D150N)
     SphI         Asn (SEQ ID NO: 5)

(Example 4B)
5'-AACGCATGCGGTAACCCATTATACAGC-3' (D150H)
     SphI        His The reverse-direction primer: (SEQ ID NO:7)

5'-GAGATACCACTTTATTTCACCCCA-3'

1 ng of plasmid pUBTZ2 (N227H) was dissolved in 100 μl of the reaction mixture of PCR (67 mM Tris-hydrochloride (pH 8.8), 16.6 mM ammonium sulfate, 6.7 mM MgCl$_2$, 10 mM 2-mercaptoethanol, 0.05 mM dATP, 0.05 mM dTTP, 0.05 mM dGTP, 0.05mM dCTP, 1 μM mutagenesis primer, 1 μM reverse-direction primer), 1 unit of Tth DNA polymerase was added. The solution was covered with one drop of mineral oil. The denaturation at 93° C. for 1 minute, the anneal at 45° C. for 1 minute and the extension at 72° C. for 45 seconds were repeated 30 times. After the reaction, the water layer was recovered, extracted with phenol and precipitated in ethanol to recover the amplified DNA (D150N-N227H (Example 4A), D150H-N227H (Example 4B)).

20 μl of reaction mixture (50 mM Tris-hydrochloride at pH 7.5, 10 mM MgCl$_2$, 100 mM NaCl, 1 mM DTT) containing half the quantity of the DNA was digested with 5 units of each SphI and AatI at 37 ° C. for 2 hours, and was treated at 70° C. for 5 minutes. The mutated SphI-AatI fragment was ligated with the 7.6 kb SphI-AatI fragment of pUBTZ2 (L144S) using a Takara Shuzo DNA ligation kit. The ligation mixture was used to transform Eschericha coli JM103 in a conventional method to give a transformant JM103/pUBTZ2 (mutant). The substituted amino acid was confirmed by the determination of the nucleotide sequence of these plasmid.

A single colony of the transformant Bacillus subtilis MT-2/pUBTZ2 (mutant) was inoculated in 5 ml of LB medium containing kanamycin (5 μg/ml) at 37° C. overnight. The culture was transferred to 500 ml of 2L medium (2% Bacto tryptone, 1% yeast extract, 0.5% NaCl) containing kanamycin (5 μg/ml) and incubated at 37° C. for 20 hours. The culture broth was centrifuged at 8,000 rpm for 30 minutes to remove bacteria, ammonium sulfate was added to the supernatant to attain 60% saturation and the mixture was stirred overnight at 4° C.

The precipitate was recovered by centrifugation and dissolved in 10 ml of the buffer (20 mM Tris-hydrochloride at pH 9.0, 10 mM CaCl$_2$). The solution was applied to 20 ml of Butyl-Toyopearl, followed by elution with the same buffer at a flow rate of 1.5 ml/minutes. Active fractions were combined and subjected to salting out with 60% saturated ammonium sulfate. The precipitate was collected by centrifugation at 15,000 rpm. for 30 minutes, and dissolved in 5 ml of the buffer (20mM Tris-hydrochloride at pH 7.5, 10mM CaCl$_2$). The enzyme solution was further applied to a gel-filtration column (TSK Gel G2000 SW 21.5×600mm), followed by elution with the same buffer at a flow rate of 1 ml/minutes. Active fractions were combined to give each purified enzyme (L144S-D150N-N227H (Example 4A), L144S-D150H-N227H (Example 4B)).

Two recombinant Bacillus subtilis strains which express the modified thermolysin-like neutral metallo-proteases according to the invention, namely, Bacillus subtilis MT-2/pUBTZ2(TZ-1) wherein the 144th leucine residue is replaced by serine, the 150th aspartic acid residue is replaced by histidine and the 227th asparagine residue is replaced by histidine, and Bacillus subtilis MT-2/pUBTZ2(TZ-2) wherein the 144th leucine residue was replaced by serine, the 150th aspartic acid residue was replaced by asparagine and the 227th asparagine residue was replaced by histidine, have been deposited at the Fermentation Research Institute, Agency of Industrial Science and Technology, Ministry of International Trade and Industry, Japan (1–3, Higashi 1-chome, Tsukuba-shi, Ibaraki, 305 Japan) under the deposition Nos. FERM BP-4112 and FERM BP-4113, respectively.

Figure 9:
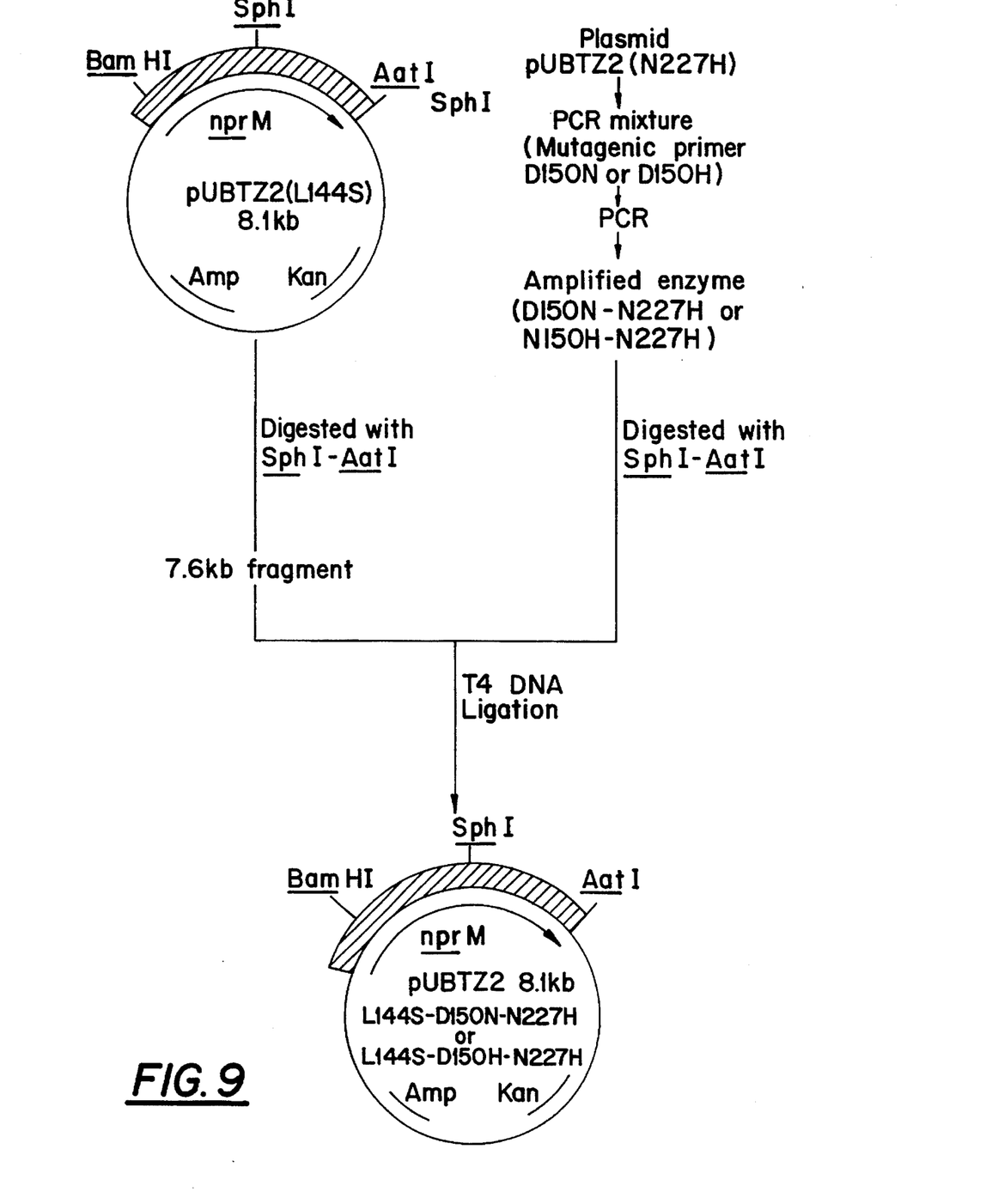
FIG. 9 shows the scheme used for constructing recombinant plasmid pUBTZ2 (mutant) (L144S-D150N-N227H or L144S-D150H-N227H) from the plasmid pUBTZ2 (L144S) and the mutagenic PCR products obtained from the plasmid pUBTZ2 (N227H) and the reaction mixture of PCR containing the mutagenesis primers (D150N).

FIG. 9 shows the scheme used for constructing recombinant plasmid pUBTZ2 (mutant) (L144S-D150N-N227H or L144S-D150H-N227H).

EXAMPLE 5

(Determination of the activity for casein digestion and Z-APM digestion)

Various modified enzymes such as N227H which represents the enzyme containing a histidine at the 227th amino acid residue (originally asparagine), N227K which represents the enzyme containing a lysine at the 227th amino acid residue (originally asparagine), N227R which represents the enzyme containing an arginine at the 227th amino acid residue (originally asparagine), L144S which represents the enzyme containing a serine at the 144th amino acid residue (originally leucine), E187Q which represents the enzyme containing a glutamine at the 187th amino acid residue (originally glutamic acid), D150N which represents the enzyme containing an asparagine at the 150th amino acid residue (originally aspartic acid), D150H which represents the enzyme containing a histidine at the 150th amino acid residue (originally aspartic acid), L144S-D150N-N227H which represents the enzyme containing a serine at the 144th position (originally leucine), an asparagine at the 150th position (originally aspartic acid), and a histidine at the 227th amino acid residue (originally asparagine) and L144S-D150H-N227H which represents the enzyme containing a serine at the 144th position (originally leucine), a histidine at the 150th position (originally aspartic acid) and a histidine at the 227th amino acid residue (originally asparagine) were used to determine the activity of casein digestion and that of Z-APM digestion.

For casein digestion method, 1 ml of each purified enzyme solution (prepared by dissolving the enzyme in 10 mM borate buffer at pH 8.0, 2 mM calcium sulfate) was added to 1 ml of substrate solution (1% casein, 1/15M phosphate buffer at pH 7.2). The mixture was incubated at 35° C. for 10 minutes, then 2.0 ml of stop solution (0.1M TCA, 0.2M sodium acetate, 0.3M acetic acid) were added, followed by further incubation at 35° C. for 30 minutes. After filtration, 5 ml of alkaline solution (0.4M sodium carbonate) and 1 ml of Folin reagent (5 times dilution of phenol reagent with distilled water) were added to 1 ml of filtrate and incubated at 35° C. for 20 minutes. The absorbance of the mixture at 660 nm was measured. One unit (PU) of the enzyme liberates from milk casein an amount of the digestion product which is capable of giving Folin's color (as determined by increase of the absorbance at 660 nm) equivalent to 1 µg of tyrosine per minute of the early stage during the reaction at 35° C., pH 7.2. Specific activity (PU/mg) was compared to wild type enzyme and the relative values are given in Table 1.

For Z-APM digestion method, 0.5 ml of each purified enzyme solution (prepared by dissolving the enzyme in 10 mM Tris-maleate buffer at pH 8.0, 10 mM calcium chloride) was added to 0.5 ml of a substrate solution (10 mM Tris-maleate at pH 8.0, 10 mM calcium chloride, 10 mM Z-APM). The mixture was incubated at 37° C. for 20 minutes, then 0.5 ml of stop solution (0.1M acetic acid) was added, followed by further addition of 1 ml of ninhydrin solution. After 15 minutes of treatment at 100° C., 2 ml of 50% ethanol was added and the absorbance was measured at 570 nm. The specific activity defined as the change in absorbance per mg of enzyme was expressed in terms of a relative value compared to that of the wild type enzyme. The results are shown in Table 1.

TABLE 1

| Enzyme | Activity for casein digestion (%) | Activity for Z-APM digestion (%) |
|---|---|---|
| N227H | 90 | 160 |
| N227K | 115 | 150 |
| N227R | 110 | 200 |
| L144S | 42 | 190 |
| E187Q | 100 | 150 |
| D150N | 120 | 130 |
| D150H | 92 | 140 |
| L144S-N227H | 41 | 300 |
| L144S-D150N | 22 | 152 |
| L144S-D150H | 29 | 184 |
| D150N-N227H | 116 | 197 |
| D150H-N227H | 107 | 324 |
| L144S-D150H-N227H (TZ-1) | 35 | 500 |
| L144S-D150N-N227H (TZ-2) | 32 | 430 |
| Wild type | 100 | 100 |

EXAMPLE 6

(Z-APM synthesising activity)

Various modified enzymes such as N227H which represents the enzyme containing a histidine at the 227th amino acid residue (originally asparagine), L144S which represents the enzyme containing a serine at the 144th amino acid residue (originally leucine), D150N which represents the enzyme containing an asparagine at the 150th amino acid residue (originally aspartic acid), D150H which represents the enzyme containing a histidine at the 150th amino acid residue (originally aspartic acid), L144S-D150N-N227H which represents the enzyme containing a serine at the 144th position (originally leucine), an asparagine at the 150th position (originally aspartic acid), and a histidine at the 227th amino acid residue (originally asparagine) and L144S-D150H-N227H which represents the enzyme containing a serine at the 144th position (originally leucine), a histidine at the 150th position (originally aspartic acid), and a histidine at the 227th amino acid residue (originally asparagine) were used to determine the Z-APM synthesizing activity.

0.1 ml of each purified enzyme solution (1 mg/ml) was added to 1 ml of a substrate solution (0.1M benzyloxycarbonyl-α-L-aspartic acid, 0.1M L-phenylalanine methyl ester hydrochloride and 0.2M Tris-maleate buffer at pH 7.0) and, after mixing, the enzymatic reaction was carried out (in a water bath) at 37° C. After 10, 20 and 30 minutes, 10 µl of each reaction mixture was sampled and analyzed by HPLC with a reverse phase column. The quantity of Z-APM produced by the enzymatic reaction was calculated, using a standard sample of Z-APM as a reference, and the specific activity per mg of enzyme was expressed in terms of relative values based on that of the wild type enzyme. The results are shown in Table 2.

TABLE 2

| Enzyme | Z-APM synthesizing activity (%) |
|---|---|
| N227H | 150 |
| L144S | 150 |
| D150N | 150 |
| D150H | 200 |
| L144S-N227H | 181 |
| L144S-D150N | 270 |
| L144S-D150H | 236 |
| D150N-N227H | 266 |
| D150H-N227H | 350 |
| L144S-D150H-N227H (TZ-1) | 500 |
| L144S-D150N-N227H (TZ-2) | 400 |
| Wild type | 100 |

EXAMPLE 7

(pH Effects on the synthesis of Z-APM of mutant enzymes)

The effect of pH on the synthesis of Z-APM were determined for both the mutant enzymes (L144S-D150H-N227H (TZ-1), L144S-D150N-N227H (TZ-2)) and wild type thermolysin-like neutral metallo-protease. The measurements were made in the same way as Example 6 except for the pH of Tris-maleate buffer (pH 5.0–8.0).

The results are shown in Table 3. The activity was represented as a relative value against the wild type enzyme at pH 7.0. The activity of Z-APM synthesis appears to be greatly influenced by the pH in the reaction mixture.

It is preferable to synthesize Z-APM at lower pH, because at lower pH less hydrolysis of the methyl ester of the substrates occurs. The present invention presents a solution to such problems in that higher enzyme activities are found at lower pH than for the wild type enzyme at its optimum pH. The activities of L144S-D150H-N227H (TZ-1) and L144S-D150N-N227H (TZ-2) at pH 6.0 are much higher than that of wild type enzyme at pH 7.0.

TABLE 3

| | Z-APM synthesizing activity (%) pH value | | | |
|---|---|---|---|---|
| Enzyme | 5.0 | 6.0 | 7.0 | 8.0 |
| L144S-D150N-N227H (TZ-1) | 23 | 274 | 517 | 154 |
| L144S-D150N-N227H (TZ-2) | 38 | 234 | 391 | 140 |

TABLE 3-continued

| Enzyme | Z-APM synthesizing activity (%) pH value | | | |
|---|---|---|---|---|
| | 5.0 | 6.0 | 7.0 | 8.0 |
| Wild type | 10 | 56 | 100 | 49 |

While the invention has been described in detail and with reference to specific examples thereof, it will be apparent to one skilled in the art that various changes can be made therein without departing from the spirits and scope thereof.

What is claimed is:

1. A modified neutral metallo-protease having the amino acid sequence of SEQ ID NO:1, wherein at least one amino acid residue selected from the group consisting of the 144th residue, leucine, the 150th residue, aspartic acid, the 187th residue, glutamic acid, and the 227 residue, asparagine, is replaced with a natural L-amino acid residue other than either said amino acid residue or a proline residue, and wherein the 150th residue is substituted with a natural L-amino acid other than an arginine residue.

2. A modified protease of claim 1, wherein the 144th residue, leucine, is replaced with a serine residue.

3. A modified protease of claim 1, wherein the 150th residue, aspartic acid, is replaced with an asparagine, histidine or lysine residue.

4. A modified protease of claim 1, wherein the 187th residue, glutamic acid, is replaced with a glutamine residue.

5. A modified protease of claim 1, wherein the 227th residue, asparagine, is replaced with a histidine, lysine or arginine residue.

6. A modified protease of claim 1, wherein the 144th residue leucine, is replaced with a serine and the 150th residue, aspartic acid, is replaced with a histidine and the 227 residue, asparagine, is replaced with a histidine residue.

7. A modified protease of claim 1, wherein the 144th residue, leucine, is replaced with a serine and the 150th residue, aspartic acid, is replaced with an asparagine and the 227th residue, asparagine, is replaced with a histidine residue.

8. A process for synthesizing benzyloxycarbonyl-α-L-aspartyl-L-phenylalanine methyl ester which comprises contacting the modified protease of any one of claims 1 to 7 with a substrate solution containing benzyloxycarbonyl-α-L-aspartic acid and L- or D,L-phenylalanine methyl ester whereby said benzyloxycarbonyl-α-L-aspartyl-L-phenylalanine methyl ester is synthesized.

* * * * *